United States Patent
Spaay et al.

(12) 
(10) Patent No.: US 6,353,204 B1
(45) Date of Patent: Mar. 5, 2002

(54) METHOD OF PRODUCING A CUTTING TOOL INSERT USING LASER CUTTING AND ION ETCHING

(76) Inventors: Paulus Gerhardus Hendrikus Maria Spaay, Watersnipstraat 32, 6601 EG Wijchen (NL); Wilhelmus Gerarda Maria Nelissen, Van Lijbdebstraat 17, 5863 BJ Blitterswijk (NL); Johannes Cornelius Franciscus Barten, Kwikstraat 36, 5831 MG Boxmeer (NL); Erik Lemmens, Elderom 31529, 5831 TM Boxmeer (NL)

(*) Notice: Subject to any disclaimer, the term of this patent is extended or adjusted under 35 U.S.C. 154(b) by 0 days.

(21) Appl. No.: 09/230,606
(22) PCT Filed: Jul. 30, 1997
(86) PCT No.: PCT/NL97/00448
  § 371 Date: Apr. 15, 1999
  § 102(e) Date: Apr. 15, 1999
(87) PCT Pub. No.: WO98/04382
  PCT Pub. Date: Feb. 5, 1998

(30) Foreign Application Priority Data

Jul. 30, 1996 (ZA) ................................. 96/6459

(51) Int. Cl.⁷ .......................... B23P 15/28; B23K 26/00
(52) U.S. Cl. .............................. 219/121.72; 219/121.85
(58) Field of Search ........................ 219/121.72, 121.85

(56) References Cited

U.S. PATENT DOCUMENTS 5,032,243 A * 7/1991 Bache et al. ............ 204/192.34
5,178,645 A * 1/1993 Nakamura et al. ............. 51/293
5,347,887 A * 9/1994 Rosenthal et al. .......... 76/104.1
5,447,208 A * 9/1995 Lund et al. .................. 175/428
5,643,523 A * 7/1997 Simpson ..................... 264/400

FOREIGN PATENT DOCUMENTS

| EP | 0101096 | * | 2/1984 |
| EP | 0 720 887 A1 | | 7/1996 |
| GB | 1544130 | * | 4/1979 |
| JP | 5-180736 | * | 7/1993 |

OTHER PUBLICATIONS

Anonymous, "Method of Sharpening Diamond Tips and Knives," Research Disclosure Jan. 1991, p. 72, No. 321110.*

* cited by examiner

*Primary Examiner*—Samuel M. Heinrich
(74) *Attorney, Agent, or Firm*—Jenkens & Gilchrist, P.C.

(57) ABSTRACT

A method of producing a cutting (30) edge on a layer (20) of diamond or other ultra-hard material includes the steps of providing a plate of the material, which plate has major flat surface (D1, D2) on opposite sides thereof, laser cutting the plate transverse to the major surfaces (D1, D2) to produce two or more layers (20) each having a cutting edge (30) defined on a surface (26) produced by the laser cut and exposing the cutting edge (30) to an ion bombardment etch. The layer of diamond or other ultra-hard material having an edge produced in this manner is useful as a tool insert, particularly a surgical blade.

11 Claims, 2 Drawing Sheets

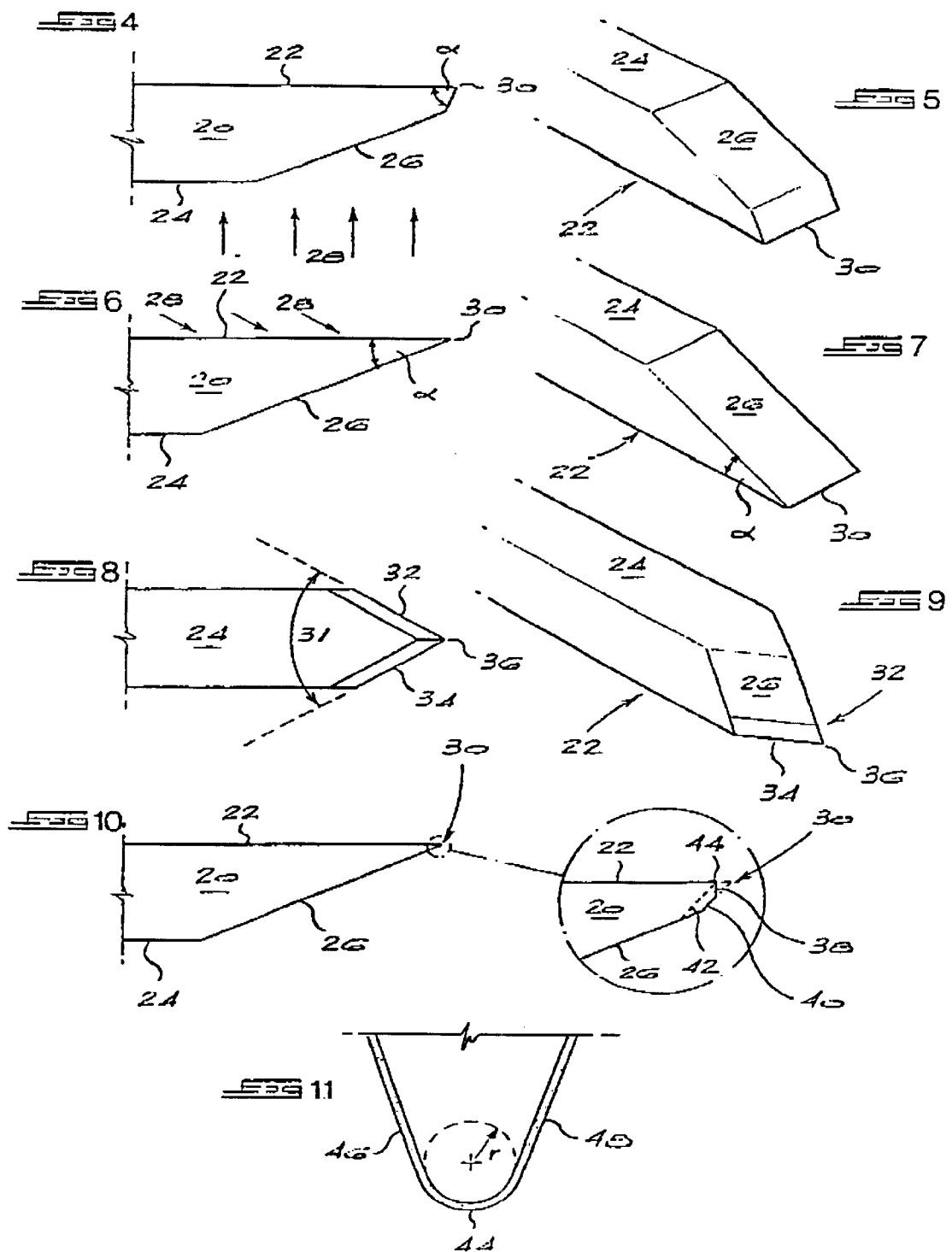

METHOD OF PRODUCING A CUTTING TOOL INSERT USING LASER CUTTING AND ION ETCHING

BACKGROUND OF THE INVENTION

This invention relates to a method of producing cutting tool inserts such as surgical blades made from single crystal or polycrystalline diamond.

Diamond has successfully been used since the early 1970's as the ultimnate material for surgical scalpels, in particular, for use in eye operations (ophrhalmology). Its hardness, strength and perfect crystalline nature allow the manufacture of cutting edges that are defect free under microscopic examination at for instance 100×magnification, as required for ophthalmology. Surgical instruments equipped with diamond scalpels outperform steel scalpels by lowering, cutting resistance and creating less deformation of the tissue being cut thus allowing better precision in the operation. This is particularly important as some operations require operating precision down to $1/100$ of a millimeter or better.

The relatively high price of natural diamond and the associated cost of processing this ultra-hard material have limited this application to certain market segments.

In recent years synthesis methods have been developed for polycrystalline diamond films at significantly lower cost than natural diamond. Even more important, it is now possible to manufacture diamond plates with a diameter of more than 10 centimeters. This makes it possible to manufacture products with much larger dimensions. Natural diamonds in sizes over, say, one centimeter are rare and very expensive. In practice, surgical scalpels are limited to sizes under 8 millimeters in length for this reason.

Although the basic properties of polycrystalline diamond make it suitable for use in surgical scalpels, the conventional methods for working monocrystalline diamond are not suitable when applied to polycrystalline material. For example, the time needed to polish a single facet on a monocrystalline scalpel is of the order of minutes. Using the same method on polycrysmlline material many hours are required thus losing the cost advantage of the material. In addition, the resulting cutting edge will fail to reach the quality required as it is extremely difficult to avoid chipping the cutting edge during the polishing process.

A practical method to shape diamond products known in the diamond industry is to laser cut the material, usually with a Nd-YAG laser beam. This method produces a typical profile as represented in FIG. 1. Referring to this figure, it can be seen that at the laser beam 10 entry side, the material edge 12 is rounded producing what is called a shoulder. When the objective is to produce a sharp cutting edge characterised by a small edge radius and an included angle of less than 60 degrees, for example, this shoulder is a disadvantage.

An alternative is to use the exit of a laser beam 14 to create a cutting edge 16 (FIG. 2). This method is the subject of EP-A-720887. This approach does produce a small edge radius and a low included angle, but the quality achieved on the exit edge is limited by irregularities in the form of waviness and a rougher facet inherent in laser cutting.

SUMMARY OF THE INVENTION

According to the present invention, a method of producing a cutting edge on a layer of ultra-hard material includes the steps of providing a plate of the material, which plate has major flat surfaces on opposite sides thereof, laser cutting the plate transverse to the major surfaces to produce two or more layers each having a cutting edge defined on a surface produced by the laser cut and exposing the cutting edge to an ion bombardment etch (also known as ion beam milling). The cutting, edge is typically defined between the surface produced by the laser cut and a major surface of the plate.

Further according, to the invention, the method includes the step of ion beam smoothing the other surface or one or both of the major surfaces of the plate prior to or after the laser cutting. It has been found that ion beam smoothing reduces the friction during cutting and can lead to an improved initial cutting edge being produced by the laser cut.

The cutting edge which is produced may be a single faceted or multifaceted curring edge. Alternatively, two or more such cutting edges may be provided. The cutting edge or edges may be straight or curved, or a combination thereof. The cutting edge may be non-symmetric or symmetric. Non-symmetric cutting edges in the context of blades are those in which one of the two intersecting surfaces forming the cutting edge is a surface of the blade itself. Symmetric cutting edges in the context of blades are edges in which neither of the two intersecting surfaces forming the cutting edge is a surface of the blade itself.

BRIEF DESCRIPTION OF THE DRAWINGS

FIGS. 4 and 5, and 6 and 7, show, respectively, sectional side views and perspective views of two embodiments of the invention, FIGS. 8 and 9 show a plan view and perspective view, respectively, of a further embodiment of the invention, FIG. 10 shows a sectional side view of a further embodiment of the invention, and FIG. 11 illustrates the apex radius of a cutting edge.

DESCRIPTION OF EMBODIMENTS

The invention has application to producing cutting blades for cutting tools and, more particularly, for diamond cutting tools. The diamond may be single crystalline or polycrystalline in nature, although the invention has greatest application with diamond which is polycrystalline in nature. The diamond may be natural, but is preferably produced synthetically, and more particularly by chemical vapour deposition (CVD).

The laser beam which is used to effect the laser cut may be any known in the art, typically a Nd-YAG beam.

Figure 3:
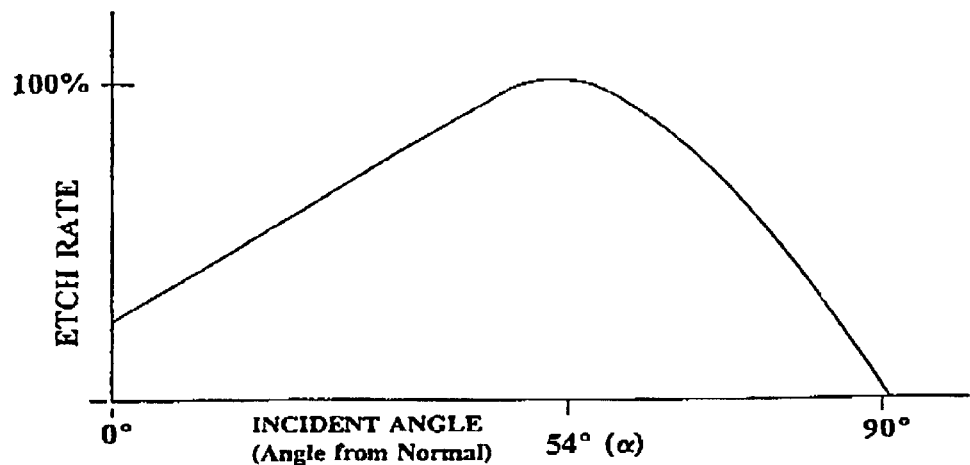
FIG. 3 is a graph illustrating the typical etch rate in relation to the incident angle of an ion bombardment etch for diamond.

The ion bombardment etch is achieved using an ion beam, preferably neutralised, with argon as the preferable gas source. The ion bombardment will etch away the material at a rate which depends on the nature of the material. In the case of diamond, the rate will be approximately 0.05 to 10 μm per hour. It has been found that the etch rate is a function of the angle of incidence. The maximum etch rate has been measured at a 54 decree incident angle, as can be seen from the graph illustrated by FIG. 3. The maximum etch rate will typically occur around 54 degrees but this angle (α) is dependent on the condition of the etch.

An example of suitable ion bombardment etch conditions using argon are a voltage of 250 to 1500 volts to accelerate the ion beam and a current density of between 0.2 mA/cm$^2$ and 20 mA/cm$^2$, these conditions being maintained for a time suitable to remove a layer of thickness between 1 and 50 μm from a surface of the material.

Conditions similar to the ion bombardment etch may be used for ion beam smoothing one or more of the surfaces of the plate or layer. The incident angle of the ion beam will typically be about 0 degrees (normal to the surface) and may be stationary or oscillating.

The invention is capable of producing very fine cutting edges and ones which have an apex radius of less than 50 nm, and preferably less than 20 nm.

The method of the invention may be used to produce a high quality, sharp cutting edge for a cutting tool insert, particularly a surgical blade. Further, the invention can also be used to improve the surface quality of a surface or facet which leads to a cutting edge. This has particular importance for surgical blades as it reduces the $t_p$ value (this is an accepted standard measure for the smoothness of a surface) of such a surface thereby reducing the blade's resistance during tissue cutting.

Figures 1, 2:
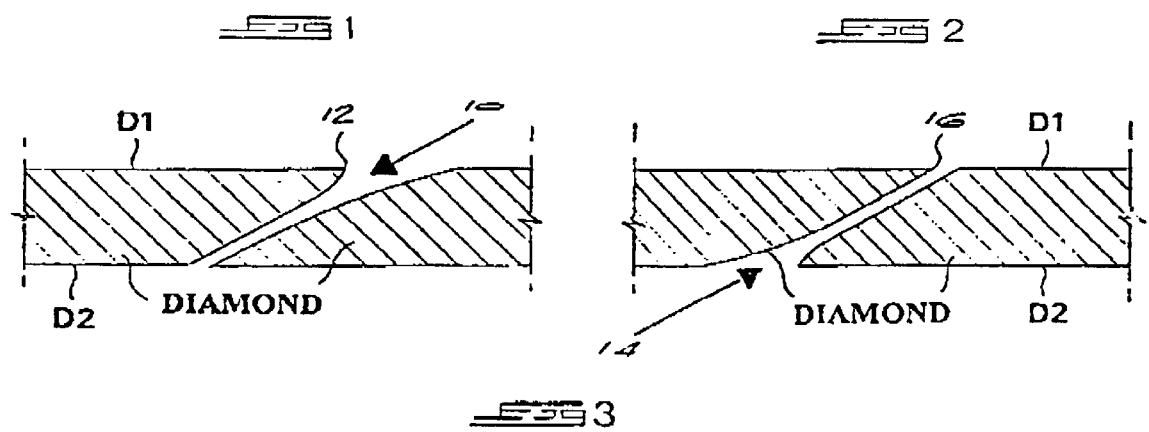
FIGS. 1 and 2 illustrate schematically a diamond plate cut by a laser beam according to the prior art.

In an embodiment of the invention, a polycrystalline CVD diamond plate is cut into two, producing two layers of polycrystalline CVD diamond as illustrated by FIG. 1 or FIG. 2. Edges of the layers, e.g edges 12 or 16, may thereafter be subjected to an ion beam etch to produce a sharp cutting edge. It is preferred that the major flat surfaces of the plates, inticated as D1 and D2 (if not polished), are ion beam smoothed prior to the laser cut being effected.

A consequence of the diamond removal that is achieved during the etching process, is that at a 0 degree incident angle, i.e. the ion beam is normal to the surface, an edge will be formed with an included angle (α), as can be seen from FIGS. 4 and 5. With reference to these Figures, a diamond cutting blade 20 has opposed flat longitudinal surfaces 22, 24 and a transverse surface 26 created by a laser cut. The ion beam, preferably a neutralised ion beam, is directed at the cutting tool in the direction of the arrows 28, i.e. normal to the sutface 24. This, as mentioned, produces an included angle (α), at the cutting edge 30. This angle is independent of the initial cross section and thus the method of the invention eliminates the laser cut shoulder and edge radius as is found in prior art laser cuts (see FIG. 1). It is possible to reduce the included angle resulting from the ion beam etch by appropriately tilting the ion beam and choosing an angle of incidence greater than 0 degrees, for example, 10 degrees. Further, the method of the invention can also be applied effectively on multifaceted products, by rotating the product during the etching process.

It is possible to reduce the included angle (α) even further, as is illustrated by FIGS. 6 and 7. In these figures, like parts to those of FIGS. 4 and 5 carry like numerals. Using an ion beam etch, a layer of material can be removed from one of the surfaces 22 leaving a substantially reduced included angle (α) and a very sharp and fine cutting edge 30. This ion beam etch also has the effect of smoothing the surface 22. The etching or smoothing may be achieved, for example, by ion etching the diamond under an incident angle, as shown by the arrows, which may be tilted parallel to or away from the cutting edge 30. The cutting edge 30 is defined between surface 22 of the blade and surface 26 produced by the laser cut and is thus a non-symmetric cutting edge. The incident angle is generally greater than 50° C. to prevent a microfacet forming on surface 22.

It is possible to produce a multifaceted cutting blade from the blade illustrated by FIGS. 4 and 5. This multifaceted blade is illustrated by FIGS. 8 and 9. Again, like parts carry like numerals. Oscillation of the ion beam in the direction of the arrow 3, and as shown in FIG. 8, produces a multifaceted blade. The multifaceted blade has cutting edges 32, 34 meeting at point 36. For the remaining numerals, parts which are similar to those in FIGS. 4 and 5 carry like numerals. Oscillation or rotation of the ion beam is needed only for angles other than zero. For zero degree etching no rotation or oscillation is necessary. Curved cutting edges may be produced in a similar manner.

A cutting edge with no waviness can be achieved by polishing a microflat on to a laser shaped cutting edge and thereafter polishing a microfacet on to the now blunt edge. This embodiment is illustrated by FIG. 10 where parts similar to those of FIGS. 4 and 5 carry like numerals. Referring to these Figures, the surface 26 produced by the laser cut may be polished to create a microflat 38 and thereafter a microfacet 40 is polished on to the now blunt edge. This polishing can be mechanical or thermomechanical. As the amount of material being removed is very small, this can be done relatively quickly. The blade is then sharpened by ion beam etching, as described above in relation to the embodiment of FIGS. 4 and 5, to remove the remnants of the small facet 40, as shown by the dotted line 42. This gives a very sharp, smooth cutting edge. The cutting edge is identified as 44. However, since the removal of material at 38 and 40 is so small, the ion beam etching effectively sharpens the cutting edge 30 defined between the laser cut surface 26 and the surface 22.

As mentioned above, the invention is capable of producing very fine cutting edges and ones which have an apex radius of less than 50 nm, and preferably less than 20 nm. For all cutting edges, no matter how fine, there will be an apex radius. This apex radius is "r" shown in FIG. 1. The cutting edge is 44 and the surfaces leading to the cutting edge are 46, 48.

What is claimed is:

1. A method of producing a cutting edge (30) on a layer (20) of diamond, said method comprising the steps of:

providing a diamond plate, said plate having major flat surfaces (D1, D2) on opposite sides thereof;

laser cutting the plate transverse to the major surfaces (D1, D2) to produce two or more layers (20) each having a cutting edge (30) defined between a transverse surface (26) produced by the laser cut and one of the major surfaces; and exposing the cutting edge (30) to an ion bombardment etch wherein an ion beam is directed at one of the major surfaces and the transverse surface, or at one of the major surfaces only.

2. A method according to claim 1 wherein one or both of the major surfaces (D1, D2) of the plate are ion beam smoothed prior to the laser cutting step.

3. A method according to claim 1 wherein the ion beam for the ion bombardment etch is neutralized ion beam.

4. A method according to claim 1 wherein the ion beam for the ion bombardment etch has an argon gas source.

5. A method according to claim 7 wherein the ion bombardment etch conditions are a voltage of 250 to 1500 volts to accelerate the ion beam and a current density of between 0.2 mA/cm$^2$ and 20 mA/cm$^2$, these conditions being maintained for a time suitable to remove a layer of thickness between 1 and 50 microns from the surface of the material.

6. A method according to claim 1 wherein the diamond plate is single crystal diamond.

7. A method according to claim 1 wherein the diamond plate is polycrystalline diamond.

8. A method according to claim 1 wherein the diamond plate is CVD diamond.

9. A method according to claim 1 wherein the ion bombardment etch removes material at a rate of 0.05 to 10 $\mu$m per hour.

10. A method according to claim 1 wherein the cutting edge produced has an apex radius of less than 50 nm.

11. A method according to claim 1 wherein the cutting edge produced has an apex radius of less than 20 nm.

* * * * *

UNITED STATES PATENT AND TRADEMARK OFFICE
CERTIFICATE OF CORRECTION

PATENT NO.    : 6,353,204 B1
DATED         : March 5, 2002
INVENTOR(S)   : Spaay et al.

It is certified that error appears in the above-identified patent and that said Letters Patent is hereby corrected as shown below:

Column 1,
Line 11, replace "ultimnate" with -- ultimate --
Line 12, replace " (ophrhalmology)" with -- (ophthalmology) --
Line 45, replace "polycrysmlline" with -- polycrystalline --

Column 2,
Line 23, replace "curring" with -- cutting --

Column 3,
Line 5, replace "decree" with -- degree --
Line 41, replace "inticated" with -- indicated --

Column 5,
Line 12, replace "according to claim 7" with -- according to claim 4 --

Signed and Sealed this

Tenth Day of December, 2002

JAMES E. ROGAN
*Director of the United States Patent and Trademark Office*